United States Patent
Fujimori et al.

(10) Patent No.: US 7,907,268 B2
(45) Date of Patent: Mar. 15, 2011

(54) SURFACE INSPECTION METHOD AND SURFACE INSPECTION DEVICE

(75) Inventors: Yoshihiko Fujimori, Yokohama (JP); Yuji Kudo, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/731,585

(22) Filed: Mar. 25, 2010

(65) Prior Publication Data

US 2010/0177312 A1   Jul. 15, 2010

Related U.S. Application Data

(63) Continuation of application No. PCT/JP2008/066528, filed on Sep. 12, 2008.

(30) Foreign Application Priority Data

Sep. 26, 2007  (JP) ................. 2007-248469

(51) Int. Cl.
*G01N 21/00* (2006.01)
(52) U.S. Cl. .................... 356/237.1; 356/237.6; 356/369
(58) Field of Classification Search .... 356/237.1–237.6, 356/364, 368, 239.3
See application file for complete search history.

(56) References Cited

U.S. PATENT DOCUMENTS

| | | | |
|---|---|---|---|
| 5,739,898 A | 4/1998 | Ozawa et al. | |
| 7,369,224 B2 * | 5/2008 | Oomori et al. | 356/237.2 |
| 2004/0063232 A1 | 4/2004 | Komatsu et al. | |
| 2005/0280806 A1 | 12/2005 | Oomori et al. | |

FOREIGN PATENT DOCUMENTS

| | | |
|---|---|---|
| JP | 04-206813 | 7/1992 |
| JP | 07-049927 | 2/1995 |
| JP | 08-250395 | 9/1996 |
| JP | 2000-206050 | 7/2000 |
| JP | 2001-108637 | 4/2001 |
| JP | 2002-280388 | 9/2002 |
| JP | 3644041 B | 2/2005 |
| JP | 3669101 B | 4/2005 |
| JP | 2006-343102 | 12/2006 |

* cited by examiner

*Primary Examiner* — Gregory J Toatley
*Assistant Examiner* — Iyabo S Alli
(74) *Attorney, Agent, or Firm* — Morgan, Lewis & Bockius LLP

(57) ABSTRACT

A surface inspection method inspects a surface of a wafer having a repeated pattern formed by double patterning. The method includes: a first step (S121) which applies an inspection light to a surface of a wafer; a second step (S122) which detects a diffracted light from the surface of the wafer to which the inspection light has been applied; and a third step (S123) which checks whether a defect is present in the repeated pattern according to the diffracted light detected in the second step. The second step detects a diffracted light corresponding to a pattern having a pitch multiplied by 2 with respect to the pitch of the repeated pattern.

19 Claims, 14 Drawing Sheets

FIG. 9
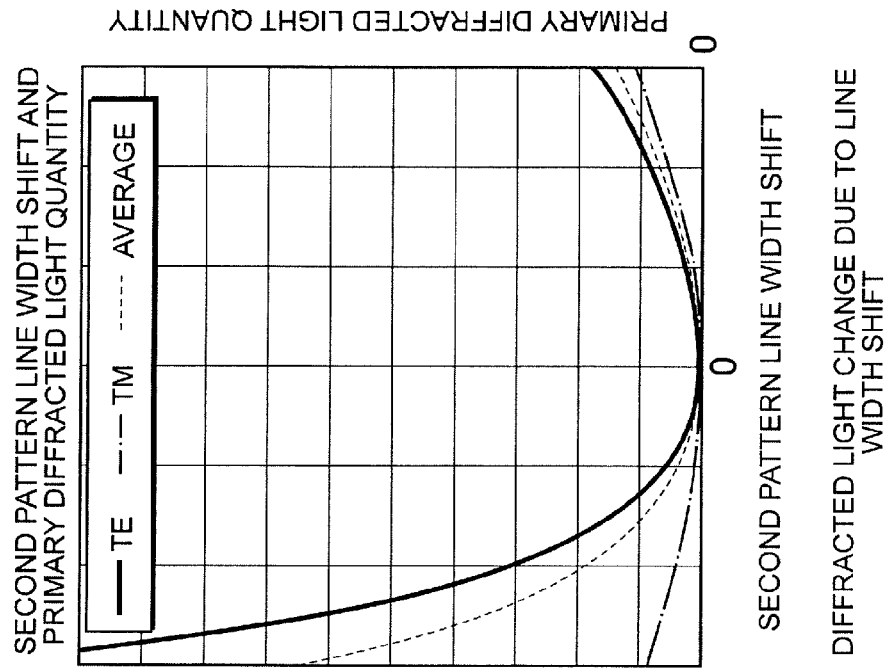
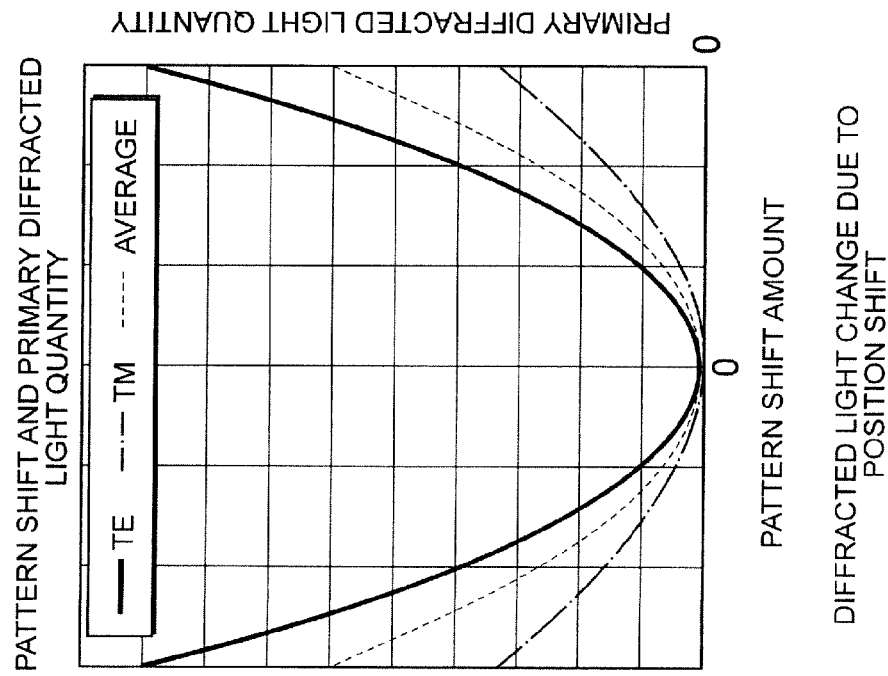

SURFACE INSPECTION METHOD AND SURFACE INSPECTION DEVICE

This is a continuation of PCT International Application No. PCT/JP2008/066528, filed on Sep. 12, 2008, which is hereby incorporated by reference. This application also claims the benefit of Japanese Patent Application No. 2007-248469, filed in Japan on Sep. 26, 2007, which is hereby incorporated by reference.

TECHNICAL FIELD

The present invention relates to a surface inspection method and device for inspecting the surface of a semiconductor wafer or the like.

TECHNICAL BACKGROUND

Available technology to inspect repeated patterns formed on a surface of a semiconductor wafer includes an inspection using the change of intensity of diffracted light that is emitted from the surface of a wafer (this type of inspection is hereafter called a "diffraction inspection"), and a method for detecting the change of polarization state caused by form birefringence of a pattern using a cross-Nicol optical system (this type of inspection is hereafter called a "PER inspection") (e.g. see Patent Documents 1 and 2). According to these inspection methods, a line width defect or cross-sectional profile defect of a pattern based on defocusing and a dose shift of the exposure devise, resist coating defect or the like can be detected at high-speed and high precision.
Patent Document 1: Japanese Patent Publication No. 3669101
Patent Document 2: Japanese Patent Application Laid-Open No. 2006-343102

DISCLOSURE OF THE INVENTION

Problems to be Solved by the Invention

However in a generation of using the half pitch 32 nm design rule for patterns formed on a semiconductor wafer, methods for forming patterns using technologies called "double patterning", "double exposure", "double development" and "spacer process" have been proposed. A problem of using these technologies is the generation of different types of defects, such as a line width shift and position shift of patterns, and a new inspection method is demanded to detect such defects.

With the foregoing in view, it is an object of the present invention to provide a surface inspection method and device that can detect specific types of defects.

Means to Solve the Problems

To achieve this object, a surface inspection method according to the present invention is a surface inspection method that inspects a surface of a target substrate having a repeated pattern with half pitch of a predetermined repeat pitch, in which a first half pattern having the predetermined repeat pitch and a second half pattern that is located in a position shifted from the first half pattern by half of the repeat pitch and that has an approximately same profile as the first half pattern are formed at least in partially different steps, having: a first step that applies an inspection light to a surface of the target substrate; a second step that detects a diffracted light from the surface of the target substrate to which the inspection light has been applied; and a third step that inspects whether a defect is present in the repeated pattern based on the diffracted light detected in the second step, and the second step further detecting the diffracted light corresponding to a pattern having a pitch multiplied by 2 or greater integer with respect to the half pitch of the repeat pitch.

It is preferable that the above mentioned surface inspection method further has: a fourth step that applies a first linearly polarized light to the surface of the target substrate; a fifth step that extracts a second linearly polarized light component, of which direction of vibration is different from the first linearly polarized light, from a reflected light from the surface of the target substrate to which the first linearly polarized light has been applied; a sixth step that detects a light quantity of the second linearly polarized light component; a seventh step that inspects whether a defect is present in the repeated pattern based on the light quantity of the second linearly polarized light component detected in the sixth step; and an eighth step that separately detects a position shift defect and a line width shift defect in the repeated pattern based on the inspection results in the third step and the seventh step.

It is preferable that the eighth step calculates a line width shift amount in the repeated pattern based on the light quantity of the second linearly polarized light component detected in the sixth step, determines that the repeated pattern has the line width shift defect if the calculated line width shift amount is greater than a first threshold, calculates a position shift amount in the repeated pattern based on the calculated line width shift amount and the diffracted light detected in the second step, and determines that the repeated pattern has the position shift defect if the calculated position shift amount is greater than a second threshold.

It is preferable that the above mentioned surface inspection method further has a pre-inspection step that inspects the surface of the target substrate in a stage when only the first half pattern of the repeated pattern is formed on the surface of the target substrate, characterized in that the surface of the target substrate is inspected using the surface inspection method according to the present invention after the second half pattern is formed on the surface of the target substrate that has been determined as a non-defective product in the pre-inspection step.

A surface inspection method according to the second aspect of the present invention is a surface inspection method that inspects a surface of a target substrate having a repeated pattern with half or less pitch of a predetermined repeat pitch which is formed according to a mask having a pattern profile with the predetermined repeat pitch, having: a first step that applies an inspection light to the surface of the target substrate; a second step that detects a diffracted light from the surface of the target substrate to which the inspection light has been applied; and a third step that inspects whether a defect is present in the repeated pattern based on the diffracted light detected in the second step, and the second step further detecting the diffracted light corresponding to a pattern having a pitch multiplied by 2 or greater integer with respect to the repeated pattern with half or less pitch of the repeat pitch.

It is preferable that the above mentioned surface inspection method further has: a fourth step that applies a first linearly polarized light to the surface of the target substrate; a fifth step that extracts a second linearly polarized light component, of which direction of vibration is different from the first linearly polarized light, from a reflected light from the surface of the target substrate to which the first linearly polarized light has been applied; a sixth step that detects a light quantity of the second linearly polarized light component; a seventh step that inspects whether a defect is present in the repeated pattern based on the light quantity of the second linearly polarized light component detected in the sixth step; and an eighth step that separately detects a position shift defect and a line width shift defect in the repeated pattern based on the inspection results in the third step and the seventh step.

It is preferable that the eighth step calculates a line width shift amount in the repeated pattern based on the light quantity of the second linearly polarized light component detected in the sixth step, determines that the repeated pattern has the line width shift defect if the calculated line width shift amount is greater than a first threshold, calculates a position shift amount in the repeated pattern based on the calculated line width shift amount and the diffracted light detected in the second step, and determines that the repeated pattern has the position shift defect if the calculated position shift amount is greater than a second threshold.

A surface inspection method according to the third aspect of the present invention has: a first step that applies an inspection light to a surface of a target substrate on which a repeated pattern is formed; a second step that detects a diffracted light from the surface of the target substrate to which the inspection light has been applied; a third step that applies a first linearly polarized light to the surface of the target substrate; a fourth step that extracts a second linearly polarized light component, of which direction of vibration is different from the first linearly polarized light, from a reflected light from the surface of the target substrate to which the first linearly polarized light has been applied; a fifth step that detects a light quantity of the second linearly polarized light component; and a sixth step that inspects whether a defect is present in the repeated pattern based on the diffracted light detected in the second step and the light quantity of the second linearly polarized light component detected in the fifth step.

It is preferable that the sixth step calculates a line width shift amount in the repeated pattern based on the light quantity of the second linearly polarized light component detected in the fifth step, determines that the repeated pattern has the line width shift defect if the calculated line width shift amount is greater than a first threshold, calculates a position shift amount in the repeated pattern based on the calculated line width shift amount and the diffracted light detected in the second step, and determines that the repeated pattern has the position shift defect if the calculated position shift amount is greater than a second threshold.

A surface inspection device according to the present invention is a surface inspection device that inspects a surface of a target substrate having a repeated pattern with half pitch of a predetermined repeat pitch, in which a first half pattern having the predetermined repeat pitch and a second half pattern that is located in a position shifted from the first half pattern by half of the repeat pitch and that has an approximately same profile as the first half pattern, are formed in at least partially different steps, having: an inspection light illumination unit that applies an inspection light to a surface of the target substrate; a diffracted light direction unit that detects a diffracted light from the surface of the target substrate to which the inspection light has been applied; and a diffracted light inspection unit that inspects whether a defect is present in the repeated pattern based on the diffracted light detected in the diffracted light detection unit, and the diffractive light detection unit detecting the diffracted light corresponding to a pattern having a pitch multiplied by 2 or greater integer with respect to the half pitch of the repeat pitch.

It is preferable that the above mentioned surface inspection device further has: a polarized light illumination unit that applies a first linearly polarized light to the surface of the target substrate; a polarized light extraction unit that extracts a second linearly polarized light component, of which direction of vibration is different from the first linearly polarized light, from a reflected light from the surface of the target substrate to which the first linearly polarized light has been applied; a polarized light detection unit that detects a light quantity of the second linearly polarized light component; a polarized light inspection unit that inspects whether a defect is present in the repeated pattern based on the light quantity of the second linearly polarized light component detected by the polarized light detection unit; and decision unit that separately detects a position shift defect and a line width shift defect in the repeated pattern based on the inspection results by the diffracted light inspection unit and the polarized light inspection unit.

It is preferable that the decision unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

A surface inspection device according to the second aspect of the present invention is a surface inspection device that inspects a surface of a target substrate having a repeated pattern with half or less pitch of a predetermined repeat pitch which is formed according to a mask having a pattern profile with the predetermined repeat pitch, having: an inspection light illumination unit that applies an inspection light to the surface of the target substrate; a diffracted light detection unit that detects a diffracted light from the surface of the target substrate to which the inspection light has been applied; and a diffracted light inspection unit that inspects whether a defect is present in the repeated pattern based on the diffracted light detected by the diffracted light detection unit, and the diffracted light detection unit detecting the diffracted light corresponding to a pattern having a pitch multiplied by 2 or greater integer with respect to the repeated pattern with half or less pitch of the repeat pitch.

It is preferable that the surface inspection device further has: a polarized light illumination unit that applies a first linearly polarized light to the surface of the target substrate; a polarized light extraction unit that extracts a second linearly polarized light component, of which direction of vibration is different from the first linearly polarized light, from a reflected light from the surface of the target substrate to which the first linearly polarized light has been applied; a polarized light detection unit that detects a light quantity of the second linearly polarized light component; a polarized light inspection unit that inspects whether a defect is present in the repeated pattern based on the light quantity of the second linearly polarized light component detected by the polarized light detection unit; and decision unit that separately detects a position shift defect and a line width shift defect in the repeated pattern based on the inspection results by the diffracted light inspection unit and the polarized light inspection unit.

It is preferable that the decision unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

A surface inspection device according to the third aspect of the present invention has: an inspection light illumination unit that applies an inspection light to a surface of a target substrate on which a repeated pattern is formed; a diffracted light detection unit that detects a diffracted light from the surface of the target substrate to which the inspection light has been applied; a polarized light illumination unit that applies a first linearly polarized light to the surface of the target substrate; a polarized light extraction unit that extracts a second linearly polarized light component, of which direction of vibration is different from the first linearly polarized light, from a reflected light from the surface of the target substrate to which the first linearly polarized light has been applied; a polarized light detection unit that detects a light quantity of the second linearly polarized light component; and an inspection unit that inspects whether a defect is present in the repeated pattern based on the diffracted light detected by the diffracted light detection unit and the light quantity of the second linearly polarized light component detected by the polarized light detection unit.

It is preferable that the inspection unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

ADVANTAGEOUS EFFECTS OF THE INVENTION

According to the present invention, specific types of defects can be detected.

BRIEF DESCRIPTION OF THE DRAWINGS

FIG. 9 are graphs depicting the intensity changes of diffracted light due to position shift and line width shift;

EXPLANATION OF REFERENCE SYMBOLS 1 surface inspection device
10 wafer (target substrate)
12 repeated pattern
16A first groove pattern (first half pattern)
16B second groove pattern (second half pattern)
20 illumination optical system (each illumination unit)
30 collective optical system
32 light receiving side polarization filter (polarized light extraction unit)
40 CCD camera (each detection unit)
41 image processing inspection unit
L1 linearly polarized light (first linearly polarized light)
L2 elliptically polarized light
L3 polarized light component
L4 linearly polarized light (second linearly polarized light)

DESCRIPTION OF THE PREFERRED EMBODIMENTS

Figure 1:
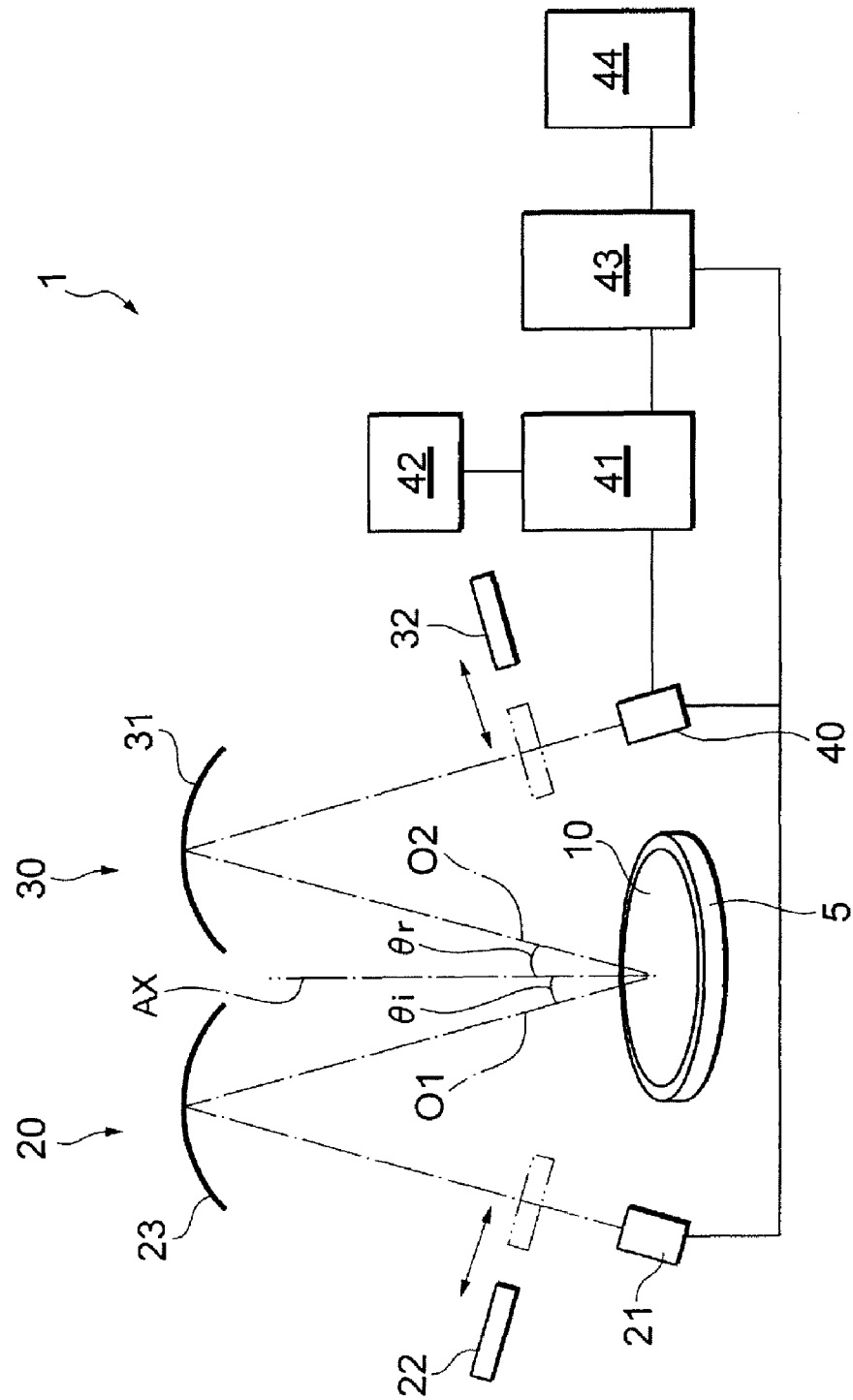
FIG. 1 is a drawing depicting a general configuration of the surface inspection device according to the present invention.

Embodiments of the present invention will now be described with reference to the drawings. FIG. 1 shows an example of a surface inspection device according to the present embodiment, and the surface defect on a semiconductor wafer 10, that is a target substrate, is inspected by this device. This surface inspection device 1 has a holder 5 that holds the wafer 10, and places the wafer 10, that is transported by a carrier device, which is not illustrated, onto the holder 5, and secures it there by vacuum suction. The holder 5 rotatably (within the surface of the wafer 10) holds the wafer 10 around the rotation axis, that is the normal line (axis AX) penetrating the center of the secured wafer 10 (center of the holder 5). The holder 5 can tilt the wafer 10 around the axis penetrating the surface of the wafer 10, so that the incident angle of the inspection illumination light (later mentioned inspection light or linearly polarized light) can be adjusted.

The surface inspection device 1 also has an illumination optical system 20 that applies an inspection illumination light to the surface of the wafer 10 secured to the holder 5, a collective optical system (a receiving optical system) 30 that collect a reflected light and diffracted light from the wafer 10 on which the inspection illumination light is received, and a CCD camera 40 that detects an image of the surface of the wafer 10 by receiving the light collected by the collective optical system 30. The illumination optical system 20 is comprised of an illumination unit 21 that has such a light source as a metal halide lamp and a mercury lamp to emit a flux of light, and an illumination system concave mirror 23 that reflects the illumination light emitted from the illumination unit 21.

The illumination unit 21 has a wavelength selection filter, which is not illustrated, so that a light having a specific wavelength can be irradiated. The illumination light, that diverges and irradiates from the illumination unit 21 onto the illumination system concave mirror 23, is transformed into approximately parallel luminous flux by the illumination system concave mirror 23, and applied to the surface of the wafer 10 held by the holder 5. At this time, the inspection illumination light to be applied to the surface of the wafer 10 is applied at an angle θi with respect to the axis AX that penetrates the center of the wafer 10 and is vertical to the surface of the wafer 10, and the light having the angle θr from the wafer 10 is received by the CCD camera 40. The relationship of the incident angle θi and the light receiving angle θr can be adjusted by tilting the holder 5. In other words, the incident angle θi to the wafer 10 can be changed as the holding angle of the wafer 10 is changed by tilting the holder 5, and the angle θr, to be received by the CCD camera 40, can also be changed accordingly.

An illumination side polarization filter 22 is placed between the illumination unit 21 and the illumination system concave mirror 23 so as to be able to be inserted into or removed from the optical path, and the diffraction inspection is performed in a state where the illumination side polarization filter 22 is removed from the optical path, and PER inspection is performed in a state where the illumination side polarization filter 22 is inserted into the optical path (the illumination side polarization filter 22 will be described in detail later).

Emitted light (reflected light or diffracted light) from the surface of the wafer 10 is collected by the collective optical system 30. The collective optical system 30 is constituted mainly by a collective system concave mirror 31 that is placed facing the direction that is at angle θr from the axis AX, and the emitted light (reflected light or diffracted light) collected by the collective system concave mirror 31 reaches the imaging plane of the CCD camera 40 via an image forming lens, that is not illustrated, and an imaging lens of the CCD camera 40, and an image of the wafer 10 is formed. As a result, the image of the surface of the wafer 10 is formed on the imaging plane of the CCD camera 40.

Between the collective system concave mirror 31 and the CCD camera 40, a light receiving side polarization filter 32 is placed so as to be able to be inserted into or removed from the optical path, and diffraction inspection is performed in a state where the light receiving side polarization filter 32 is removed from the optical path, and PER inspection is performed in a state where the light receiving side polarization filter 32 is inserted into the optical path (the light receiving side polarization filter 32 will be described later).

The CCD camera 40 performs photo-electric transformation on the image of the surface of the wafer 10 formed on the imaging plane so as to generate image signals, and outputs the image signals to an image processing inspection unit 41. A memory 42 and a sequence control unit 43 are electrically connected to the image processing inspection unit 41, and an image display device 44 is electrically connected to the sequence control unit 43. The image processing inspection unit 41 transforms the image of the wafer 10 into a predetermined depth (e.g. an 8 bit) digital image based on the image signal of the wafer 10, that is input from the CCD camera 40. In the memory 42, the digital image of the wafer 10, acquired by the image processing inspection unit 41, and the device conditions (tilt angle) at this time, are stored.

In the memory 42, an image of a non-defective wafer (not illustrated) is stored in advance, and when the image of the wafer 10 (digital image) is generated, the inspection unit 41 compares the image of the wafer 10 and the image of the non-defective wafer, and inspects whether a defect is present on the surface of the wafer 10. Then the inspection result by the image processing inspection unit 41 and the image of the wafer 10 at this time are output to and displayed on the image display device 44 via the sequence control unit 43. The sequence control unit 43 systematically controls the operation of the holder 5, illumination unit 21, CCD camera 40, image processing inspection unit 41 and image display device 44.

Figure 2:
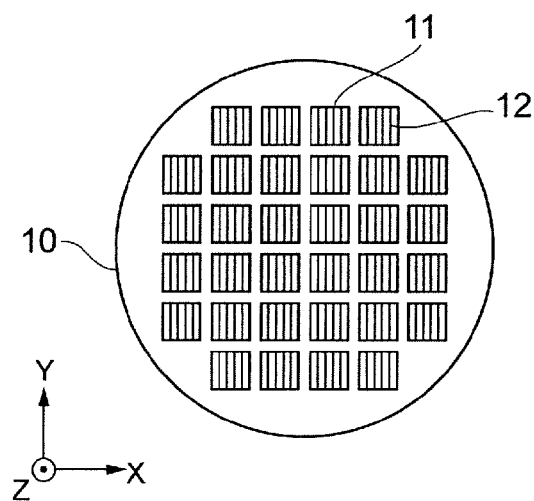
FIG. 2 is an external view of a surface of a semiconductor wafer.
Figure 3:
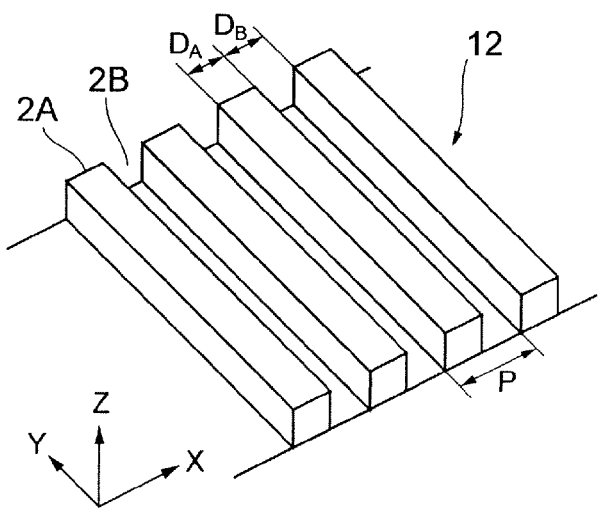
FIG. 3 is a perspective view depicting the bump structure of a repeated pattern.

On the surface of the wafer 10, a plurality of chip areas 11 are arrayed in the X and Y directions, as shown in FIG. 2, and a predetermined repeated pattern 12 is formed in each chip area. The repeated pattern 12 is a resist pattern (e.g. interconnect pattern) where a plurality of line portions 2A are arrayed with a predetermined pitch P along the lateral direction (X direction) thereof as shown in FIG. 3. A portion between adjacent line portions 2A is a space portion 2B. The array direction of the line portion 2A (X direction) is called the "repeat direction of the repeated pattern 12". The design value of the line width $D_A$ of the line portion 2A in the repeated pattern 12 is assumed to be ½ of the pitch P (that is, a 0.5 duty).

In the present embodiment, the above mentioned repeated pattern 12 is formed by technologies called "double patterning", "double exposure", "double development" and "spacer process" (hereafter called "double patterning"). The repeated pattern 12 of the present embodiment is assumed to be a repeated pattern with a 32 nm half pitch, where the line width $D_A$ of the line portion 2A is 32 nm, and the line width $D_B$ of the space portion 2B is 32 nm, in order to simplify description.

Figure 4A:
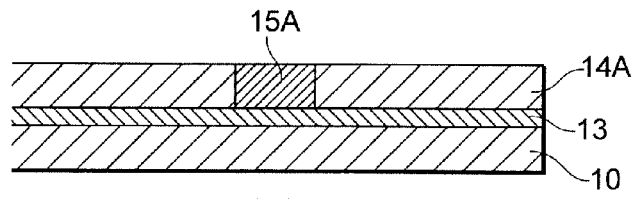
FIG. 4 are diagrams depicting an example of double patterning.
Figure 4B:
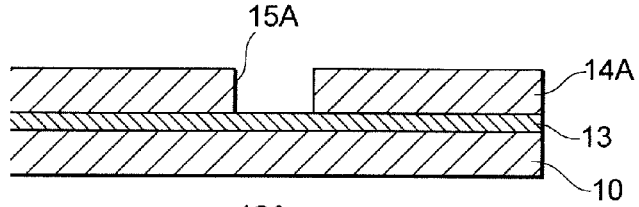
Figure 4C:
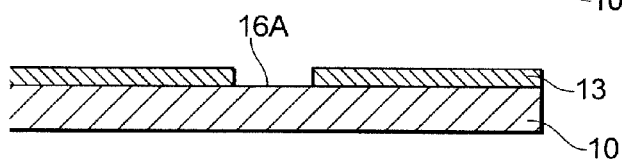

According to the pattern generation based on "double patterning", resist 14A is coated on the wafer 10 on which a hard mask layer 13 has been formed, and a pattern 15A of which line width is 32 nm, pitch is 128 nm and duty is 0.25, is exposed and developed, as shown in FIG. 4A, whereby a first resist pattern 15A is formed, as shown in FIG. 4B. Then using the resist 14A (unexposed portion) as a mask, the hard mask layer 13 is etched, and then the resist 14A is removed, whereby the hard mask layer 13 having a first groove pattern 16A (that is a first half pattern) of which line width is 32 nm, pitch is 128 nm and duty is 0.25, as shown in FIG. 4C, is formed.

Figure 4D:
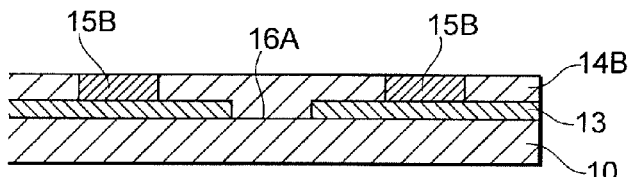
Figure 4E:
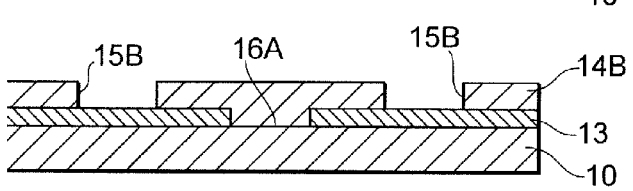
Figure 4F:
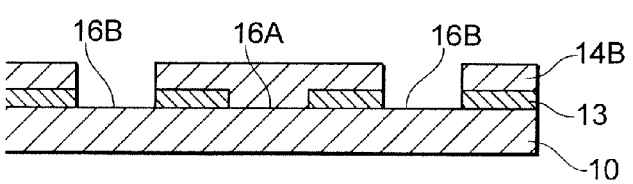
Figure 4G:
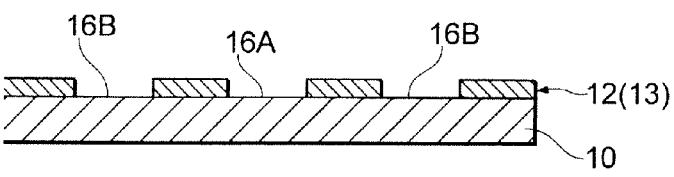

Then resist 14B is coated on the hard mask layer 13 having a first groove pattern 16A, and a pattern 15B, of which line width is 32 nm, pitch is 128 nm and duty is 0.25, is exposed and developed in a position that is 64 nm (half pitch of the first groove pattern 16A) shifted from the first resist pattern 15A (first groove pattern 16A), as shown in FIG. 4D, whereby a second resist pattern 15B is formed, as shown in FIG. 4E. Then the hard mask layer 13 is etched using the resist 14B (unexposed portion) as a mask, whereby the second groove pattern 16B (that is second half pattern), which has the same shape as the first pattern 16A, is formed at a position shifted from the first groove pattern 16A by 64 nm, as shown in FIG. 4F. By removing the resist 14B, the first groove pattern 16A and the second groove pattern 16B are combined, as shown in FIG. 4G, and a repeated pattern 12 (hard mask layer 13), of which line width is 32 nm, pitch is 64 nm and duty is 0.5, is formed.

Pattern generation according to the "double exposure" method will be described briefly as follows: a pattern of which line width is 32 nm, pitch is 128 nm and duty is 0.25 is exposed twice with a 64 nm shift, and a repeated pattern of which line width is 32 nm, pitch is 64 nm and duty is 0.5 is acquired by performing development (and etching) once. A specific method of "double exposure" is described in detail in Japanese Patent Publication No. 3644041 (Nikon). Pattern generation according to a "double development" method will be described briefly as follows: a pattern of which line width is 64 nm, pitch is 128 nm and duty is 0.5 is exposed once, and the positive development (removing the portion in which light intensity is high) and the negative development (removing the portion in which light intensity is low) are combined, so as to acquire a repeated pattern of which line width is 32 nm, pitch is 64 nm and duty is 0.5. An example of the pattern generation based on the "spacer process" method for which some types have been proposed, is a pattern of which line width is 32 nm, pitch is 128 nm and duty is 0.25 exposed once and film is deposited on this pattern, and a similar pattern is formed on the side wall portion of the film (gap between films which are shifted from the pattern by 64 nm).

Figure 5A:
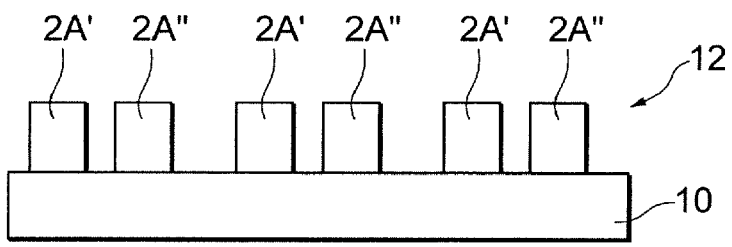
FIG. 5 are diagrams depicting an example of patterns where position shift and line width shift are generated.
Figure 5B:
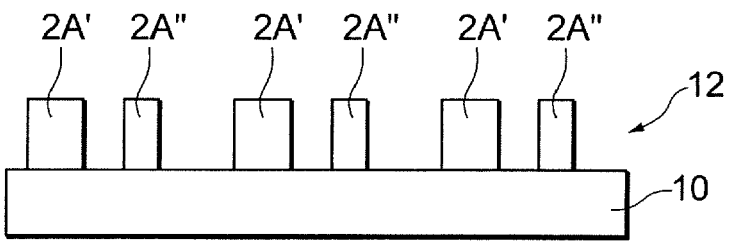

If such a double patterning technology is used, defects that are different from conventional ones are generated. One is an error of the positional relationship between an odd pattern (line portion 2A') and an even pattern (line portion 2A"), as shown in FIG. 5A (hereafter called "position shift"). Another one is a difference of line widths (or difference of cross-sectional profiles) between an odd pattern (line portion 2A') and an even pattern (line portion 2A"), as shown in FIG. 5B (hereafter called "line width shift").

These defects could be partially inspected by conventional diffraction inspection or PER inspection, but a highly accurate inspection cannot be performed, nor can a position shift and line width shift be detected separately.

Figure 6:
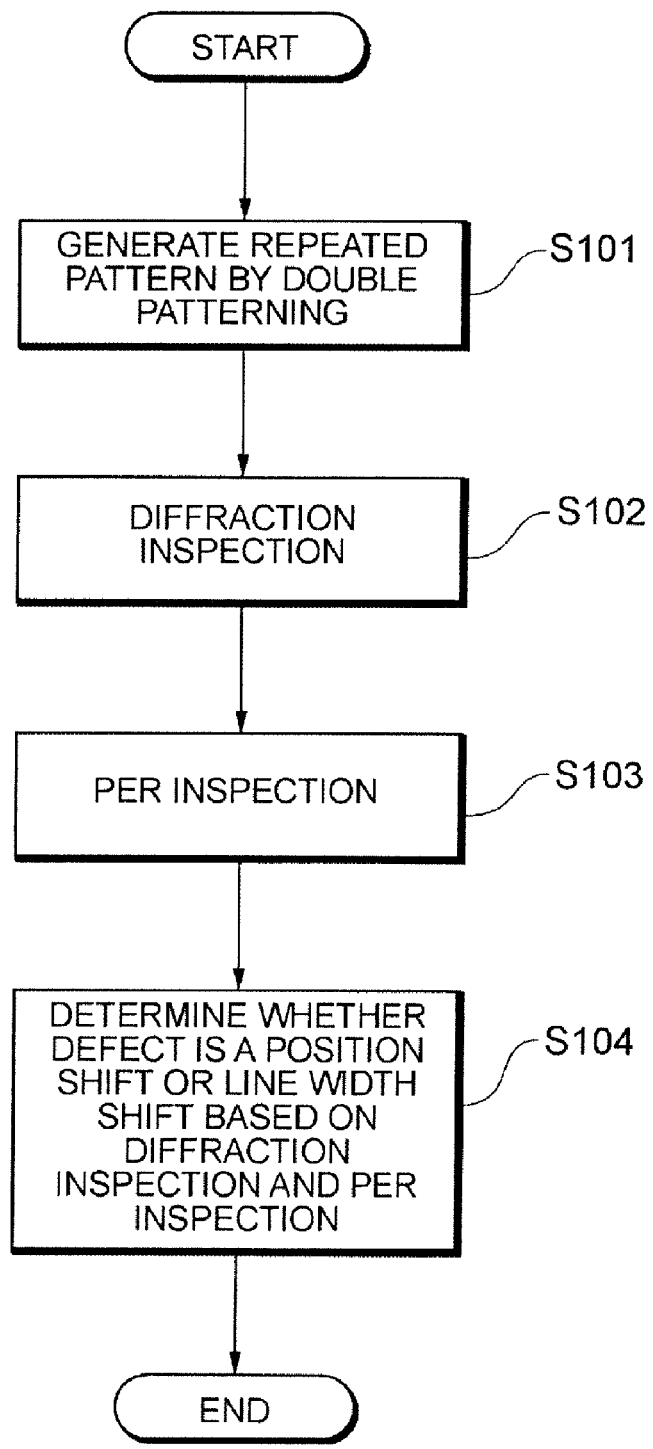
FIG. 6 is a flow chart depicting the surface inspection method according to the present invention.

According to the present embodiment, however, the position shift and line width shift can be detected separately by combining the diffraction inspection and PER inspection. The surface inspection method using the surface inspection device 1 according to the present embodiment will now be described with reference to the flow chart in FIG. 6.

Prior to the surface inspection of the wafer 10, a repeated pattern 12 of which line width is 32 nm, pitch is 64 nm and duty is 0.5, is formed on the surface of the wafer 10 by the above mentioned double patterning (step S101).

After the repeated pattern 12 is formed on the surface of the wafer 10, diffraction inspection is performed on the surface of the wafer 10 (step S102). When diffraction inspection is performed, it is set such that the following Expression (1) is satisfied, where P denotes a pitch of the pattern, λ denotes a wavelength of an inspection light that is applied to the surface of the wafer 10, θi is incident angle of the inspection light, and θr is an exit angle of the diffracted light of n-th order (light receiving angle of the CCD camera 40).

$$P \times \{\sin(\theta r) - \sin(\theta i)\} = \pm n \times \lambda \quad (1)$$

According to the present embodiment, wavelength λ of the inspection light or incident angle θi and light receiving angle θr (that is the tile angle of the holder 5) is set so that the CCD camera 40 receives the diffracted light of n-th order that corresponds to a pattern having a pitch P of 128 nm, that is, double the pitch of the repeated pattern 12 (which is equal to half pitch of the repeated odd number pattern or even number pattern). If the repeated pattern 12 is formed normally, as shown in FIG. 3, and neither the position shift nor the line width shift is generated, the diffracted light corresponding to a pattern having a 128 nm pitch is not generated. However if a position shift or a line width shift is periodically generated, as shown in FIG. 5, diffracted light corresponding to a pattern having a 128 nm pitch is generated. This is because the repeated pattern 12 becomes the repeated pattern having a 128 nm pitch (double pitch), that is a combination of the odd patterns and even patterns, and the detected image (diffraction inspection image) at this time has a signal intensity distribution according to the position shift and line width shift (according to the light quantity of the detected light).

FIG. 9 shows the change of light quantity of the diffracted light based on an optical simulation. In FIG. 9, TE is a polarized light having an oscillating component that is parallel with the pattern, and TM is a polarized light having an oscillating component that is vertical to the pattern, and the average indicates non-polarized light. As is understood from above, diffraction inspection can be performed even with non-polarized light, but diffraction inspection with higher sensitivity can be performed if polarized light, that has higher sensitivity, is used. In the following description, it is assumed that the diffraction inspection is performed with non-polarized light, in order to avoid confusion with the PER inspection, but the present invention is effective even if polarized light is used.

Even if the repeated pattern 12 is formed normally, in some cases diffracted light may be generated. If the characteristics of the pattern are different (e.g. complex refractive index is different) between the odd pattern and even pattern depending on the technology of double patterning, diffractive light may be generated even if the repeated pattern has been generated normally. In this case, signal intensity distribution of the detected image (diffraction inspection image) in a normal case is stored in advance, and a difference from the stored signal intensity distribution becomes the signal intensity change that indicates an abnormality.

Figure 7:
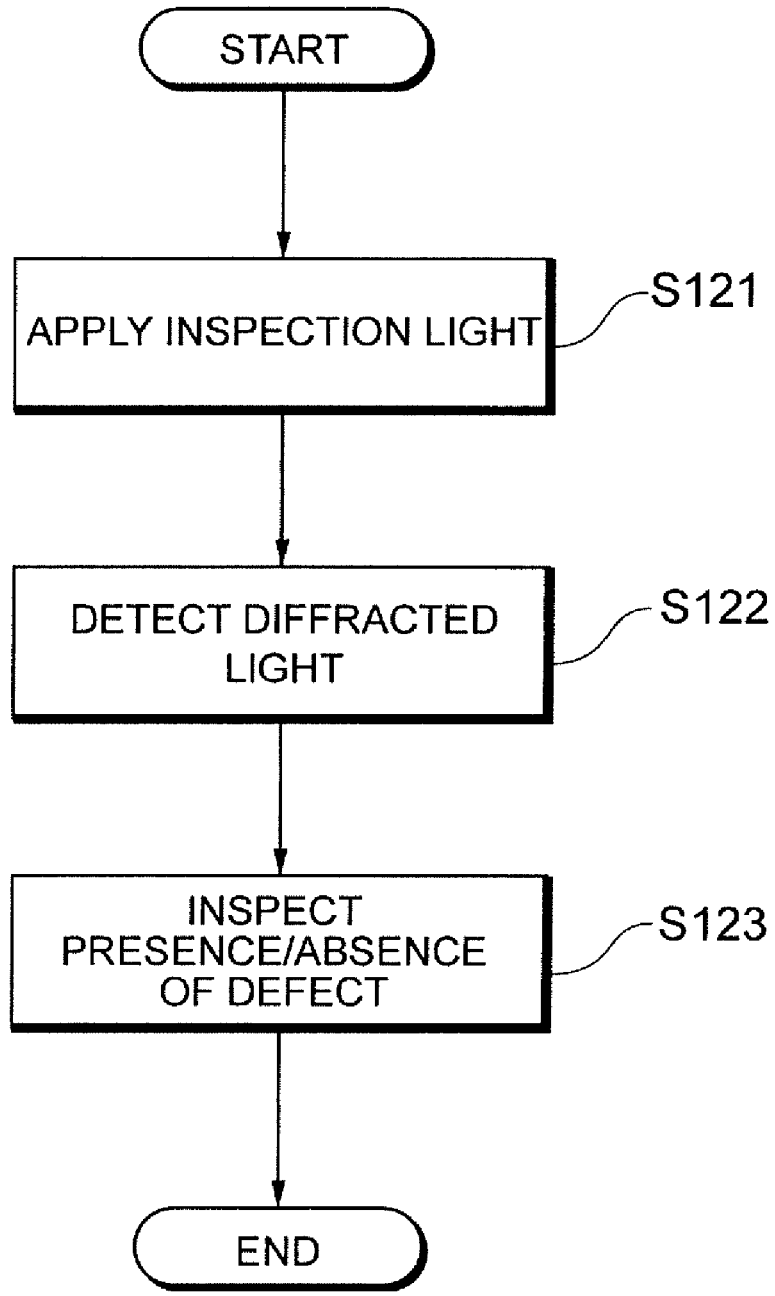
FIG. 7 is a flow chart depicting a diffraction inspection.

According to the flow of the diffraction inspection to be described with reference to the flow chart shown in FIG. 7, the inspection light is applied to the surface of the wafer 10, that is the target substrate, in a state where the illumination side polarization filter 22 and the light receiving side polarization filter 32 are removed from the optical path (see the solid line in FIG. 1) (step S121). At this time, the illumination light that diverges and irradiates from the illumination unit 21 onto the illumination system concave mirror 23 becomes parallel luminous flux, that is inspection light, by the illumination system concave mirror 23, and is applied to the surface of the wafer 10 held by the holder 5, but as mentioned above, the wavelength and incident angle of the inspection light are set such that the CCD camera 40 receives the diffracted light corresponding to the pattern having a 128 nm pitch.

Then the diffracted light (e.g. $1^{st}$ order diffracted light) that is emitted from the surface of the wafer 10, to which the inspection light is applied, is detected (step S122). The diffracted light emitted from the surface of the wafer 10 at this time is collected by the collective system concave mirror 31 of the collective optical system 30, and forms an image on the imaging plane of the CCD camera 40. The CCD camera 40 photo-electrically transforms the diffracted image of the surface of the wafer 10, that is formed on the imaging plane, to generate image signals, and outputs the image signals to the image processing inspection unit 41.

Based on the diffracted light detected in the previous step, it is inspected whether a defect is present in the repeated pattern 12 (step S123). At this time, the image processing inspection unit 41 compares the signal intensity level of the image of the wafer 10 (generated by the diffracted light) that is input from the CCD camera 40 with the signal intensity level of the image of the non-defective wafer (generated by the diffracted light) stored in the memory 42, and determines whether a defect is present when the change amount of the signal intensity level exceeds the predetermined threshold.

After diffraction inspection is performed as mentioned above, PER inspection is continuously performed on the surface of the wafer 10 (step S103).

As mentioned above, the design value of the line width $D_A$ of the line portion 2A in the repeated portion 12 is assumed ½ of pitch P. If the repeated pattern 12 is formed exactly as the design value, the line width $D_A$ of the line portion 2A and the line width $D_B$ of the space portion 2B become the same, and the volume ratio of the line portion 2A and the space portion 2B becomes approximately 1:1. If the exposure dose or focus to generate the repeated pattern 12 deviates from the optimum value, on the other hand, the pitch P does not change, but the line width $D_A$ of the line portion 2A becomes different from the design value, and also becomes different from the line width $D_B$ of the space portion 2B, and the volume ratio between the line portion 2A and the space portion 2B deviates from the approximately 1:1.

In PER inspection, a defect of the repeated pattern 12 is inspected using the change of the volume ratio between the line portion 2A and the space portion 2B in the repeated pattern 12, as mentioned above. To simplify the description, it is assumed that an ideal volume ratio (design value) is 1:1. The change of the volume ratio is due to deviation of the exposure dose or the focus from an optimum value, and appears in each shot area of the wafer 10. The volume ratio can also be reworded as the area ratio of the cross-sectional profiles.

In PER inspection, the illumination side polarization filter 22 and the light receiving side polarization filter 32 are inserted into the optical path (see the two-dot chain line in FIG. 1), and a signal is detected when the repeated pattern 12 is generated normally, and this signal intensity level does not change even if a position shift, shown in FIG. 5A, is generated, but the signal intensity changes only according to the line width shift shown in FIG. 5B. The principle of PER inspection will be sequentially described along with the configuration of the device which performs PER inspection.

As mentioned above, the holder 5 holds the wafer 10 that can be rotated around the axis AX as a rotation axis, and can rotate the repeat direction of the repeated pattern 12 (X direction in FIG. 2 and FIG. 3) on the wafer 10 within the surface of the wafer 10. When PER inspection is performed, the holder 5 maintains the wafer 10 in the horizontal state, and rotate it to a predetermined rotation position, and holds the repeat direction of the repeated pattern 12 on the wafer 10 to be a diagonal 45° from the later mentioned incident plane of the illumination light (traveling direction of the illumination light).

The illumination side polarization filter 22 is placed between the illumination unit 21 and the illumination system concave mirror 23, and the transmission axis thereof is set in a predetermined direction, so that the light from the illumination unit 21 is transformed to the linearly polarized light according to the transmission axis. At this time, the illumination system concave mirror 23 transforms the light transmitted through the illumination side polarization filter 22 into parallel luminous flux, and illuminates the wafer 10, that is a target substrate. In this way, the light from the illumination unit 21 is transformed into the first linearly polarized light L1 (see FIG. 11A) via the illumination side polarization filter 22 and the illumination system concave mirror 23, and is applied to the entire surface of the wafer 10.

The traveling direction of the first linearly polarized light L1 (direction of the principal ray of the linearly polarized light L1 that reaches an arbitrary point on the surface of the wafer 10) is approximately parallel with the optical axis O1 from the illumination unit 21. The optical axis O1 transmits through the center of the holder 5, and is inclined from the normal line (axis AX) that passes through the center of the holder 5 by a predetermined angle (θi).

Figures 11A, 11B, 11C:
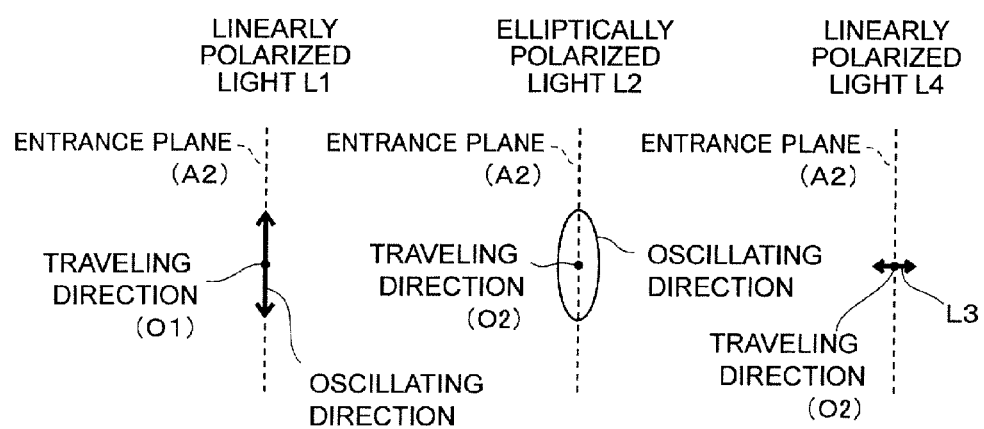
FIG. 11 are diagrams depicting direction of vibration s of the linearly polarized light and elliptically polarized light.

The first linearly polarized light L1 is incident on the wafer 10 as p-polarized light. In other words, as FIG. 11A shows, the plane that includes the traveling direction of the linearly polarized light L1 and the direction of vibration of the electric vector (plane of vibration of the linearly polarized light L1) is included in the incident plane A1 of the linearly polarized light L1. The plane of vibration of the linearly polarized light L1 is specified by the transmission axis of the illumination side polarization filter 22. The incident angle of the linearly polarized light L1 at each point of the wafer 10 is the same because of the parallel light, and corresponds to the angle (θi) formed by the optical axis O1 and the normal line (axis AX).

Figure 10:
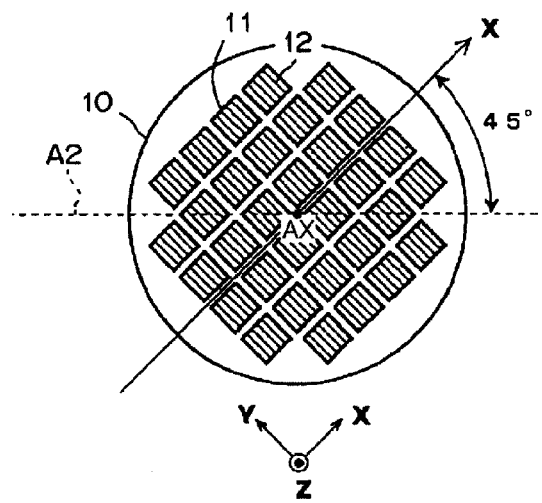
FIG. 10 is a diagram depicting the inclination state between the incident plane of linearly polarized light and the repeat direction of a repeated pattern.

The linearly polarized light L1 that is incident on the wafer 10 is the p-polarized light, so if the repeat direction (X direction) of the repeated pattern 12 is set to be a 45° angle from the incident plane A2 of the linearly polarized light L1 (traveling direction of the linearly polarized light L1 on the surface of the wafer 10), as shown in FIG. 10, then the angle formed by the direction of the plane of vibration of the linearly polarized light L1 and the repeat direction (X direction) of the repeated pattern 12 on the surface of the wafer 10 is also set to 45°.

In other words, the first linearly polarized light L1 is incident on the repeated pattern 12 such that the direction of the plane of vibration (V direction in FIG. 12) of the linearly polarized light L1 on the surface of the wafer 10 diagonally crosses the repeated pattern 12 in a state of tilting 45° from the repeat direction (X direction) of the repeated pattern 12.

Figure 12:
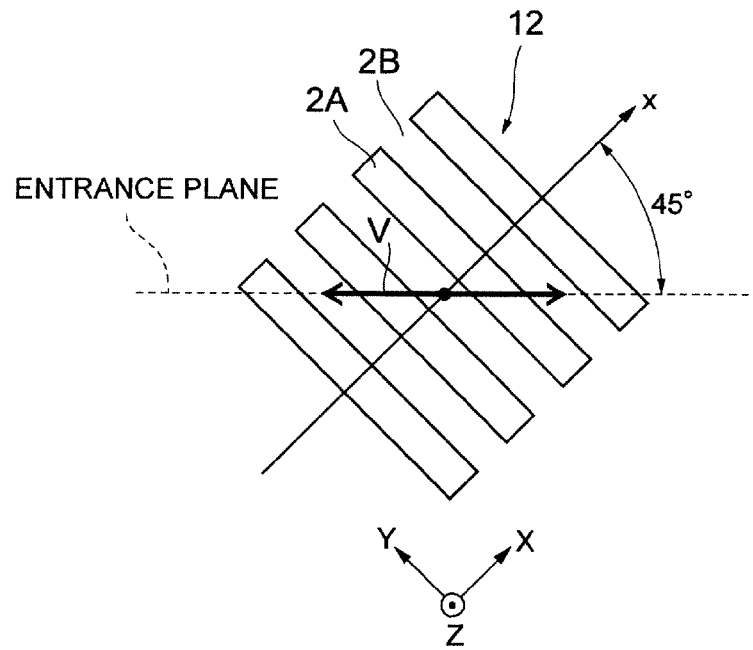
FIG. 12 is a diagram depicting the inclination state between the direction of the plane of vibration of the linearly polarized light and the repeat direction of a repeated pattern.

This state of the angle between the first linearly polarized light L1 and the repeated pattern 12 is the same throughout the entire surface of the wafer 10. The state of the angle between the first linearly polarized light L1 and the repeated pattern 12 is the same even if the angle is 135°, 225° or 315°, instead of the above mentioned 45°. The angle formed by the direction of the plane of vibration (V direction) and the repeat direction (X direction) in FIG. 12 is set to 45° to maximize the sensitivity of the defect inspection of the repeated pattern 12.

When the first linearly polarized light L1 is applied to the repeated pattern 12, an elliptically polarized light L2 is generated from the repeated pattern 12 in the regular reflection direction (see FIG. 11B). In this case, the traveling direction of the elliptically polarized light L2 matches the regular reflection direction. The regular reflection direction is a direction that is included in the incident plane A2 of the linearly polarized light L1, and is inclined by an angle equal to the incident angle (θi) of the linearly polarized light L1 (θr=θi).

Figure 13:
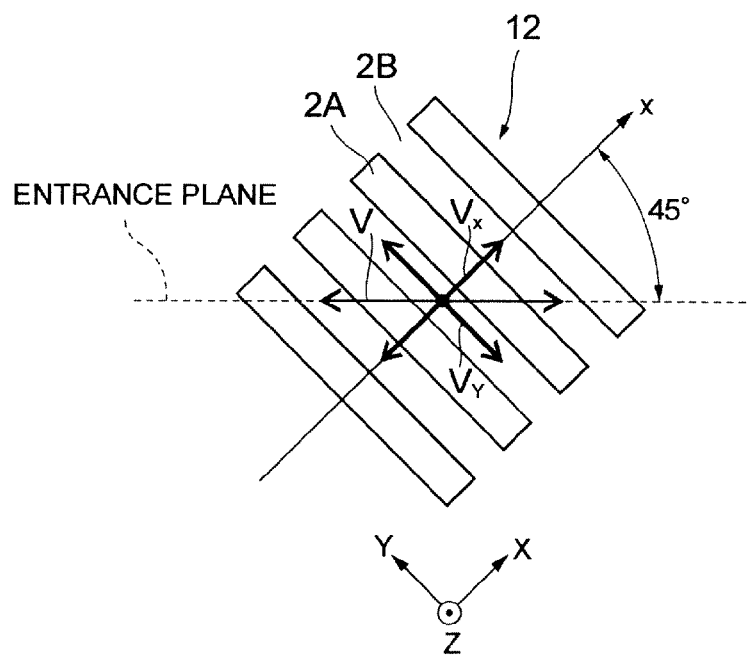
FIG. 13 is a diagram depicting the state of the direction of the plane of vibration of the linearly polarized light separating into a polarized light component that is parallel with the repeat direction and a polarized light component that is vertical to the repeat direction.

It will now be described in brief why the first linearly polarized light L1 is elliptically polarized by being reflected on the repeated pattern 12, and the elliptically polarized light L2 is generated from the repeated pattern 12. When the first linearly polarized light L1 is incident on the repeated pattern 12, the direction of the plane of vibration (V direction in FIG. 12) is split into two polarized light components Vx and Vy, as shown in FIG. 13. One polarized light component Vx is a component parallel with the repeat direction (X direction). The other polarized light component Vy is a component that is vertical to the repeat direction (X direction). The two polarized light components Vx and Vy independently receive a different amplitude change and phase change respectively. The amplitude change and phase change are different because the complex refractive index is different between Vx and Vy due to the anisotropy of the repeated pattern 12, and this is called "form birefringence". As a result, the reflected lights of the two polarized light components Vx and Vy have a different amplitude and phase from each other, and the reflected light formed by a combination thereof becomes elliptically polarized light L2 (see FIG. 11B).

The degree of elliptical polarization, due to the anisotropy of the repeated pattern 12, can be regarded as the polarized light component L3 (see FIG. 11C) that is vertical to the plane of vibration of the linearly polarized light L1 shown in FIG. 11A, out of the elliptically polarized light L2 shown in FIG. 11B. The magnitude of the polarized light component L3 depends on the material and shape of the repeated pattern 12 and the angle formed by the direction of the plane of vibration (V direction) and the repeat direction (X direction) in FIG. 12. Therefore in the case of maintaining the angle formed by the V direction and the X direction at a predetermined value (45° in the present embodiment), the degree of elliptical polarization (magnitude of the polarized light component L3) changes if the profile of the repeated pattern 12 changes, even if the material of the respected pattern 12 is predetermined.

Figure 14:
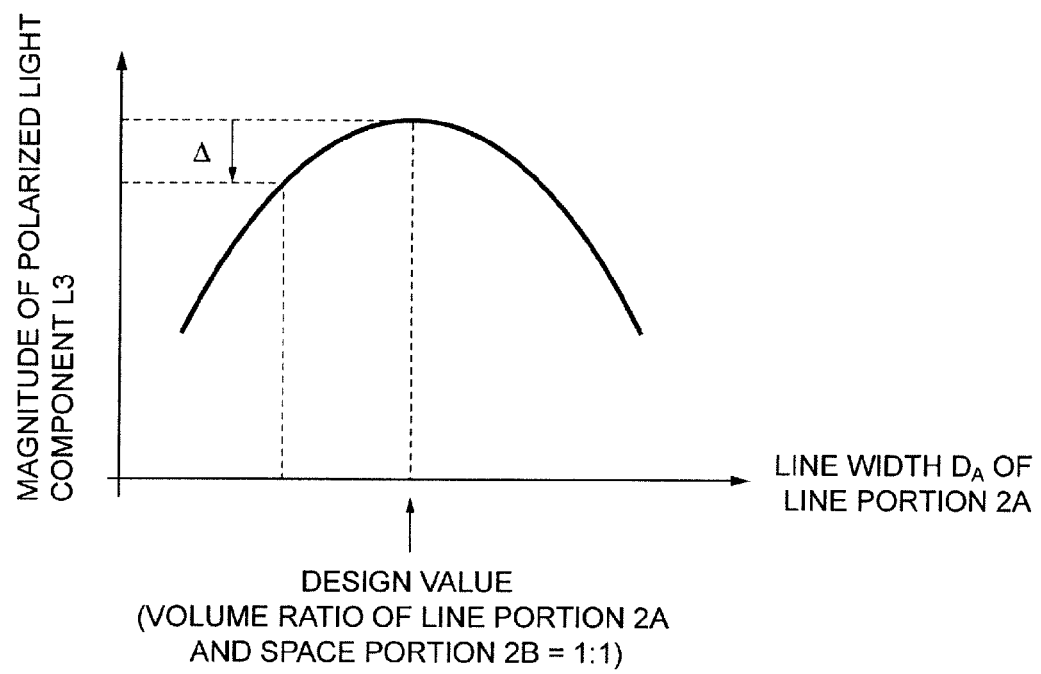
FIG. 14 is a graph depicting the relationship between the magnitude of the polarized light component and the line width of the line portion of a repeated pattern.

The relationship between the profile of the repeated pattern 12 and the magnitude of the polarized light component L3 will be described. As FIG. 3 shows, the repeated pattern 12 has a bumpy profile in which line portion 2A and space portion 2B are alternately arrayed along the X direction, and if the repeated pattern 12 is formed exactly according to the design values by optimum exposure focal length, the line width $D_A$ of the line portion 2A and the line width $D_B$ of the space portion 2B are the same, and the volume ratio between the line portion 2A and the space portion 2B becomes approximately 1:1. It is defined that the magnitude of the polarized light component L3, in the case of this ideal profile, is G. If the exposure focal length deviates from the optimum value, the volume ratio between the line portion 2A and the space portion 2B deviates from the approximately 1:1. In this case, the magnitude of the polarized light component L3 has been changed compared with G, that is, the ideal case. FIG. 14 shows an example of the change of the magnitude of the polarized light component L3. The abscissa in FIG. 14 is a line width $D_A$ of the line portion 2A.

If the repeated pattern 12 is illuminated by the first linearly polarized light L1 in a state where the direction of the plane of vibration (V direction) in FIG. 12 is inclined 45° from the repeat direction (X direction) of the repeated pattern 12, the elliptically polarized light L2, that is generated by the first linearly polarized light L1 reflecting in the regular reflection direction, has a degree of elliptical polarization (magnitude of the polarized light component L3 in FIG. 11C) that is according to the profile of the repeated pattern 12 (volume ratio between the line portion 2A and the space portion 2B). The traveling direction of the elliptically polarized light L2 is included in the incident plane A2 of the linearly polarized light L1, and is inclined to be symmetric with the traveling direction of the linearly polarized light L1 (θr=θi) with respect to the normal line (axis AX) that passes through the center of the holder 5.

The optical axis O2 of the collective optical system 30 is set to be inclined from the normal line (axis AX) that passes through the center of the holder 5, by the angle θr (=θi). Therefore the elliptically polarized light L2 that is a reflected light from the repeated pattern 12 advances along the optical axis O2.

The light receiving side polarization filter 32 is placed between the collective system concave mirror 31 of the collective optical system 30 and the CCD camera 40, and transmits the regular reflected light from the surface of the wafer 10 so as to transform it into the second linearly polarized light L4 (see FIG. 11C). The direction of the transmission axis of the light receiving side polarization filter 32 is set to be vertical to the transmission axis of the above mentioned illumination side polarization filter 22. In other words, the transmission axis is set such that the direction of vibration of the second linearly polarized light L4 in the plane vertical to the traveling direction of the second linearly polarized light L4 becomes perpendicular to the direction of vibration of the first linearly polarized light L1 in the plane vertical to the traveling direction of the first linearly polarized light L1. In other words, the illumination side polarization filter 22 and the light receiving side polarization filter 32 constitute a cross-Nicol system.

Therefore when the elliptically polarized light L2 transmits through the light receiving side polarization filter 32, only the linearly polarized light L4, corresponding to the polarized light component L3 in FIG. 11C of the elliptically polarized light L2, is extracted, and is guided to the CCD camera 40. As a result, the reflected image of the wafer 10 is formed on the imaging plane of the CCD camera 40 by the second linearly polarized light L4. The brightness of the reflected image of the wafer 10 is approximately in proportion to the light intensity of the linearly polarized light L4, and changes according to the profile of the repeated pattern 12.

Figure 8:
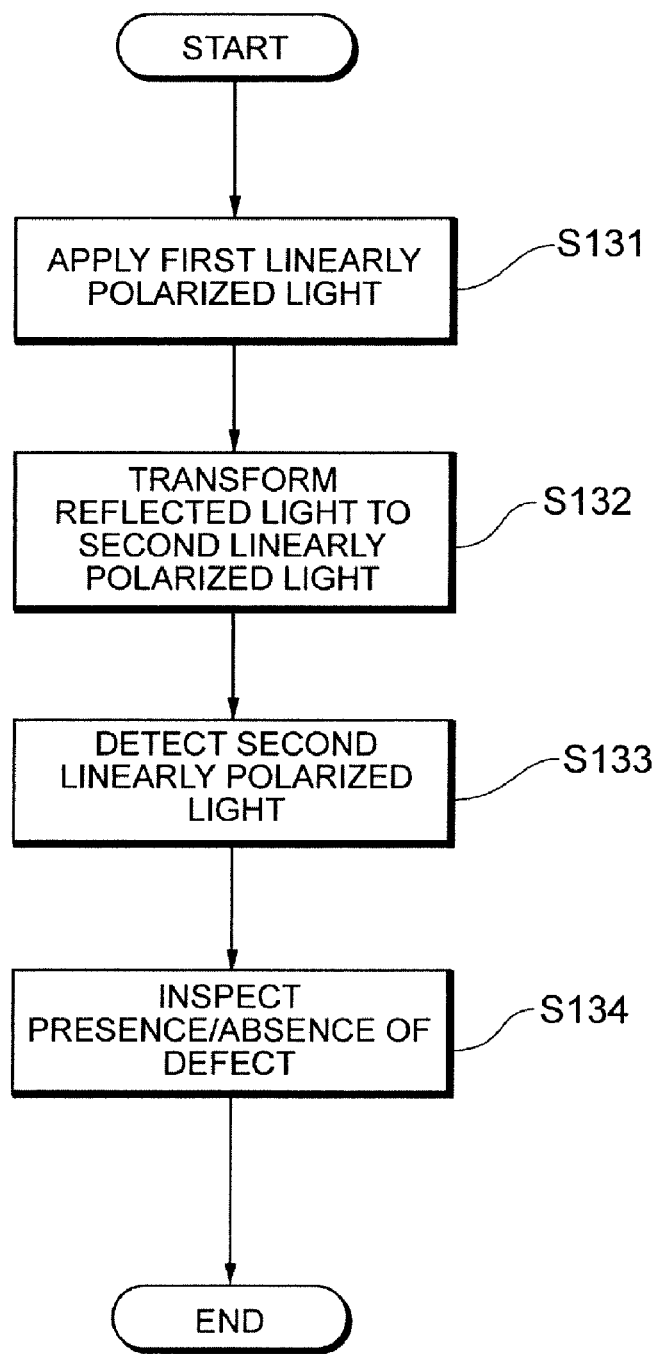
FIG. 8 is a flow chart depicting a PER inspection.

According to the flow of PER inspection, which is described with reference to the flow chart shown in FIG. 8, the first linearly polarized light L1 is applied to the surface of the wafer 10, which is a target substrate, in a state where the illumination side polarization filter 22 and the light receiving side polarization filter 32 are inserted into the optical path (see the two-dot chain line in FIG. 1) (step S131). At this time, the illumination light emitted from the illumination unit 21 is transformed into the first linearly polarized light L1 in the illumination side polarization filter 22, and becomes parallel light by the illumination optical system 23, which is applied to the surface of the wafer 10.

The regularly reflected light (elliptically polarized light L2) reflected on the surface of the wafer 10 is collected by the collective system concave mirror 31 of the collective optical system 30, and the elliptically polarized light L2 is transformed into the second linearly polarized light L4 by the light receiving side polarization filter 32, and is guided to the CCD camera 40 (step S132). Then the second linearly polarized light L4, guided to the CCD camera 40, is detected by the CCD camera 40 (step S133). At this time, the CCD camera 40 generates image signals by the photoelectric-transform of the reflected image of the wafer 10 that is formed on the imaging plane by the second linearly polarized light L4, and outputs the image signals to the image processing inspection unit 41.

Based on the second linearly polarized light L4 detected in the previous step, it is inspected whether a defect is present in the repeated pattern 12 (step S134). At this time, the image processing inspection unit 41 compares the signal intensity level of the image of the wafer 10 (generated by the second linearly polarized light L4), that is input from the CCD camera 40, with the signal intensity level of the image of the non-defective wafer (generated by the second linearly polarized light L4) that is stored in the memory 42, and determines that a defect is present if the change amount of the signal intensity level exceeds a predetermined threshold.

After this PER inspection is performed, the image processing inspection unit 41 determines whether the defect is a position shift or line width shift based on the result of the diffraction inspection and PER inspection (step S104). If the presence of a defect is determined in the diffraction inspection or PER inspection, a position shift or line width shift can be discerned. This is because the diffraction inspection has sensitivity for both the position shift and the line width shift, but the PER inspection has sensitivity only for a line width shift. In other words, firstly, if a defect is detected only in the diffraction inspection, the defect is a position shift. Secondly, if a defect is detected in both direction inspection and PER inspection, the defect is a defect of a line width shift, or a defect of a line width shift and a position shift.

Therefore if the relationship of the signal intensity change amount in the diffraction inspection image and PER inspection image and the line width shift amount and the position shift amount of a pattern is checked and stored in the memory 42 in advance, the line width shift amount and the position shift amount can be determined by calculation. In concrete terms, the line width shift amount and the position shift amount are determined as follows.

First a test wafer (not illustrated), on which shots of which the position shift amount and line width shift amount are intentionally changed in steps and are arrayed in a matrix, is created, and the diffraction inspection image and PER inspection image of this test wafer are acquired to measure the signal intensity change amount for each shot. By approximating this measured data by functions, the following relational expressions are determined in advance.

First the relationships of the signal intensity change amount and the line width shift amount/position shift amount in the diffraction inspection image are determined according to the following Expressions (2) and (3).

$$dk = KSW(ds, dw) \quad (2)$$

$$ds = KSW^{-1}(dk, dw) \quad (3)$$

Here ds denotes a position shift amount, dw denotes a line width shift amount, dk denotes a signal intensity change amount in the diffraction inspection image, and KSW denotes a function of ds and dw. And $KSW^{-1}$ denotes a function (of dk and dw) when KSW is transformed, and can be determined from KSW.

Next, the following Expressions (4) and (5) are determined for the relationship of the signal intensity change amount and line width shift amount in the PER inspection image.

$$dp = PW(dw) \quad (4)$$

$$dw = PW^{-1}(dp) \quad (5)$$

Here dp denotes a signal intensity change amount in the PER inspection image, and PW denotes a function of dw. And $PW^{-1}$ denotes a function (of dp) when PW is transformed, and can be determined from PW.

Based on the diffraction inspection image and PER inspection image obtained in step S102 and step S103, the signal intensity change amount dk in the diffraction inspection image and the signal intensity change amount dp in the PER inspection image are determined, and the line width shift amount dw is determined based on the signal intensity change amount dp in the PER inspection image using Expression (5), then the position shift amount ds is determined based on the line width shift amount dw determined above and the signal intensity change amount dk in the diffraction inspection image, using Expression (3).

A method to determine Expressions (2) to (5) is not limited to a method of using a test wafer, but may be a calculation method based on optical theory using a refractive index, film thickness and line width of the material of the pattern, and the refractive index and film thickness of the substrate. $KSW^{-1}$ (KSW) and $PW^{-1}$ (PW) are functions, but a lookup table, that is a table of input parameter values and output parameter values, may be used instead functions. If a value the same as the input parameter value to be calculated does not exist in the lookup table, then a corresponding output value is determined by neighboring data and interpolation.

As a result, according to the surface inspection device 1 and method of the present embodiment, diffracted light corresponding to a pattern having a pitch (128 nm) that is double the pitch (64 nm) of the repeated pattern 12, is detected to inspect the surface of the wafer 10, so that a light quantity change (signal intensity change) according to the position shift and line width shift can be detected, and such a defect as position shift and line width shift, generated by double patterning, can be detected.

By combining the PER inspection which has a sensitivity only for a line width shift, with diffraction inspection which has sensitivity for both position shift and line width shift, the position shift and line width shift can be detected separately.

In the above mentioned embodiment, the presence/absence of a defect may be determined in step S104, instead of deciding the presence/absence of a defect in step S102 and step S103. In concrete terms, in this case, the line width shift amount dw is calculated based on the signal intensity change amount dp of the second linearly polarized light L4 detected in step S103 (using Expression (5)), and it is detected that a defect of the line width shift exists if the calculated line width shift amount dw is greater than a predetermined (first) threshold, and the position shift amount ds is calculated based on the line width shift amount dw calculated above and the signal intensity change amount dk of the diffracted light detected in step S102 (using Expression (3)), and it is determined that a defect of position shift exists if the calculated position shift amount ds is greater than a predetermined (second) threshold. In this way the surface can be inspected at higher accuracy.

Now a variant form of the surface inspection method will be described with reference to the flow chart in FIG. 15. In this variant form, it is assumed that the repeated pattern 12 is formed by the "double patterning" method. First in step S201, resist 14A is coated on the wafer 10 on which a hard mask layer 13 has been formed, and the pattern 15A of which line width is 32 nm, pitch is 128 nm and duty is 0.25 is exposed and developed, as shown in FIG. 4A, so as to form the first resist pattern 15A, as shown in FIG. 4B.

In the next step S202, the surface of the first resist pattern 15A formed in step S201 is inspected. At this time, the diffraction inspection or PER inspection corresponding to the pattern having the 128 nm pitch is performed on the first resist pattern 15A, and the surface is inspected according to a conventional method.

In the next step S203, the hard mask layer 13 is etched using the resist 14A (unexposed portion) as a mask, and the resist 14A is removed. Then a hard mask layer 13 having a first groove pattern 16A (that is, the first half pattern) of which line width is 32 nm, pitch is 128 nm and duty is 0.25, is formed, as shown in FIG. 4C.

In the next step S204, the surface of the hard mask layer 13, having the first groove pattern 16A, is inspected. At this time, the surface is inspected by a conventional method, such as the diffraction inspection or PER inspection on the hard mask layer 13 having the first groove pattern 16A corresponding to the 128 nm pitch.

In the next step S205, the resist 14B is coated on the hard mask layer 13 having the first groove pattern 16A, and the second resist pattern 15B, of which line width is 32 nm, pitch is 128 nm and duty is 0.25, is exposed and developed in a position shifted 64 nm from the first resist pattern 15A (first groove pattern 16A), as shown in FIG. 4D, so as to form the second resist pattern 15B, as shown in FIG. 4E.

In the next step S206, the surface of the second resist pattern 15B, formed in step S205, is inspected. At this time, the surface is inspected by a conventional method, such as the diffraction inspection or PER inspection corresponding to a pattern having a 128 nm pitch on the second resist pattern 15B.

In the next step S207, the hard mask layer 13 is etched using the resist 14B (unexposed portion) as a mask, and the resist 14B is removed. Then, as FIG. 4F shows, the second groove pattern 16B (that is, the second half portion) having a profile the same as the first groove pattern 16A is formed in a position that is shifted 64 nm from the first groove pattern 16A, and as FIG. 4G shows, the first groove pattern 16A and the second groove pattern 16B are combined, and a repeated pattern 12 (hard mask layer 13), of which line width is 32 nm, pitch is 64 nm and duty is 0.5, is formed.

After the repeated pattern 12 (hard mask layer 13) is formed on the surface of the wafer 10, the diffraction inspection is performed on the surface of the wafer 10 in the next step S208. This diffraction inspection is performed by the same method as the above mentioned step S102.

After diffraction inspection is performed on the surface of the wafer 10, PER inspection is performed on the surface of the wafer 10 in the next step S209. This PER inspection is performed by the same method as the above mentioned step S103.

After PER inspection is performed on the surface of the wafer 10, it is determined whether the defect is a position shift or line width shift based on the results of the diffraction inspection and PER inspection in the next step S210. This step is executed by the same method as the above mentioned step S104.

By this surface inspection method, a similar effect as the above mentioned embodiment can also be implemented. As for the position shift detected in steps S208 to S210, an average value of the line widths on the surface area of the wafer 10 corresponding to 1 pixel of an image is reflected in the signal intensity distribution of the image. This means that if the pattern generated first (e.g. first groove pattern 16A) is formed thin, and the pattern generated second (e.g. second groove pattern 16B) is formed thick, then the average may indicate that no change occurred to the line width. Therefore it is preferable to inspect that the pattern is correctly generated in the first patterning. Step S204 is performed for this reason.

If a defect is detected in the inspection in the stage of the resist pattern, the wafer of which defect is detected can be reworked (saved) by stripping the resist and coating resist again, and performing exposure and development. The surface inspection (steps S202 and S206) is performed for each resist pattern 15A and 15B for this reason.

Figure 15:
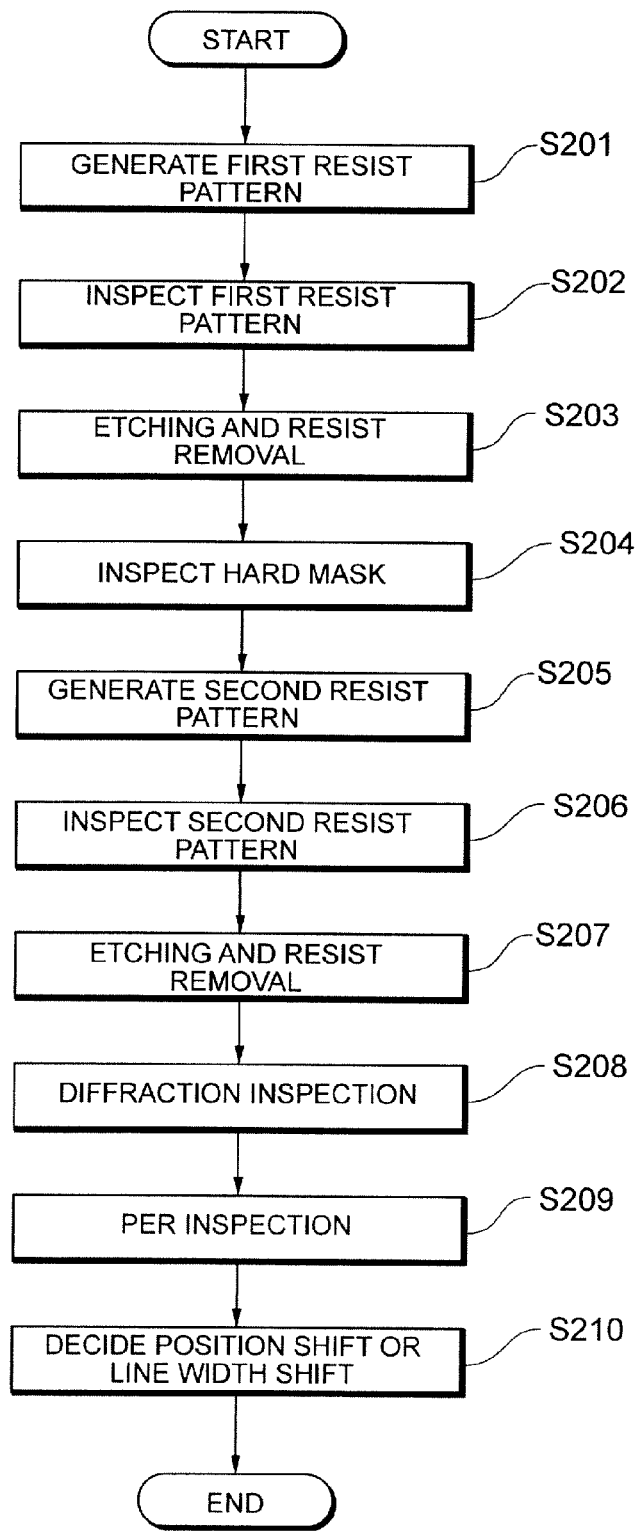
FIG. 15 is a flow chart depicting a variant form of the surface inspection method.

In the flow chart shown in FIG. 15, there are 6 steps in which surface inspection is performed. In the stage of developing a processing of the semiconductor fabrication steps, or in the early stage of mass production, it is preferable to perform inspection according to all or most of the steps, but once a mass production line is stabilized, it is preferable to omit steps to perform surface inspection, only considering the timing where a defect tends to occur. In concrete terms, it is possible that a step to perform surface inspection itself is omitted, or a ratio of wafers for which surface inspection is performed is decreased.

In the above mentioned variant form, "double patterning" was described as an example, but similar surface inspection can be performed even if a different pattern technology is used. In this case, some inspection steps may not be required, depending on the type of patterning technology.

In the case of "double exposure", for example, development is performed once, and since all patterns have already been formed after development, the inspection is required only for steps S208 to S210. In this case, if the resist pattern is inspected, a defective wafer can be reworked. In the case of "double development", the inspection in steps S208 to S210 are performed basically after development is performed twice. In this case, a defective wafer can be reworked if the resist pattern is inspected. The inspection may be performed after the first development. In the case of "spacer process", it is preferable that the same inspection as step S202 is performed for the pattern generated first, then the same inspection as steps A208 to S210 are performed for the pattern generated finally.

The surface inspection method and device according to the present invention is effective for a technology in which a position shift and a line width shift could occur between an odd pattern and even pattern, even if the technology does not use "double patterning", "double exposure", "double development" and "spacer process". The surface inspection method and device according to the present invention is not limited to the repeated pattern having a 32 nm half pitch, but can be effective if a repeated pattern has been formed by double patterning.

The repeated pattern generated by double patterning is not limited to a repeated pattern of which odd pattern and even pattern are formed in different steps, but may be a repeated pattern of which odd pattern and even pattern are partially formed in different steps, and in the same processing for the remainder of the steps.

For example, as Japanese Patent Application Laid-Open No. H8-250395 discloses, positive resist is coated on the substrate and then a line and space pattern is exposed on the positive resist, and after the positive resist is developed, an exposed portion of the resist is removed, and negative resist is coated on the space portion of the positive resist that is formed after the removal of the resist. Then after exposing and developing the area including the boundary portion of the positive resist and negative resist, the exposed portion of the positive resist and unexposed portion of the negative resist are removed, whereby a repeated pattern, in which the odd pattern is constituted by positive resist and the even pattern is constituted by negative resist, for example, is formed. In this way, a repeated pattern may be formed using different steps until the positive resist and negative resist are coated, and then using the same processing for subsequent steps of exposure, development and removal. In this case, if the center of the opening of the mask to expose the area, including the boundary portion of the positive resist and negative resist, is not located on the boundary portion, the line width of the repeated pattern becomes uneven, and the position of each pattern is also shifted cyclically. If the pitch of the opening of the mask and the size of the opening are not in a predetermined relationship as well, a similar defect is generated.

Figure 16A:
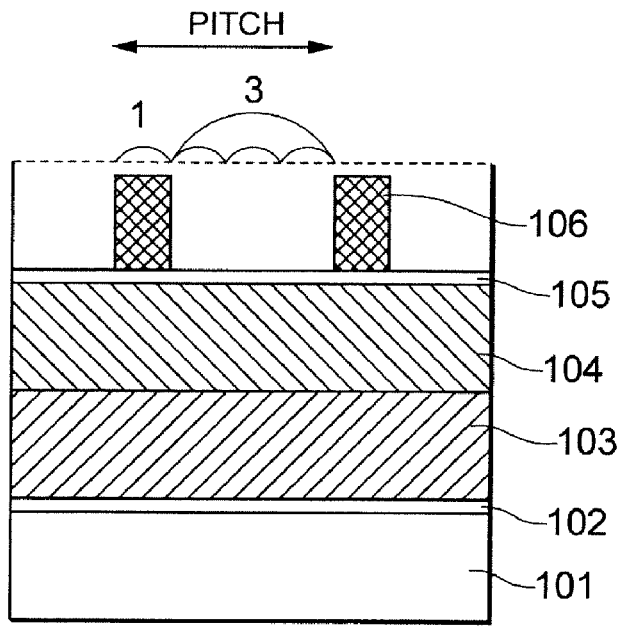
FIG. 16 are diagrams depicting a variant form of the repeated pattern.
Figure 16B:
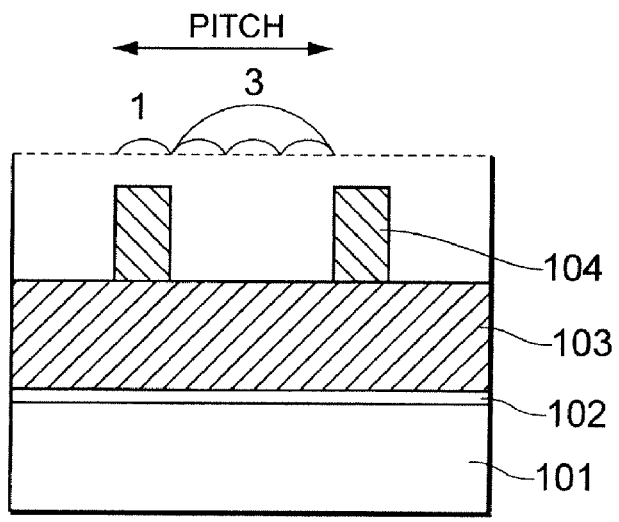
Figure 17A:
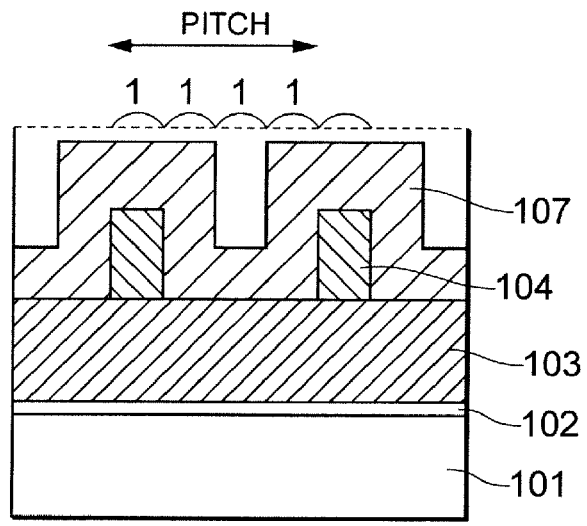
FIG. 17 are diagrams depicting a variant form of the repeated pattern.
Figure 17B:
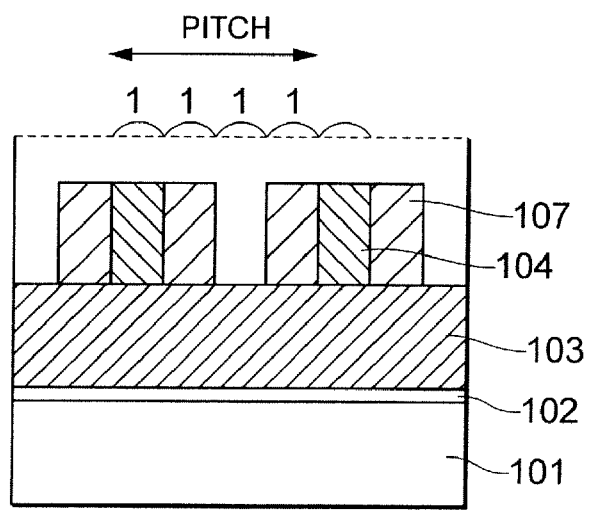

For the repeated pattern generated by double patterning, the odd pattern and even pattern may be formed via a same step. For example, as Japanese Patent Application Laid-Open No. 2002-280388 discloses, a first insulation film 102, gate interconnect material film 103, second insulation film 104, anti-reflection film 105 and photoresist 106 are sequentially layered on a substrate 101, and a mask of which ratio of the line portion and space portion is 1:3 is patterned on the photo resist 106 (see FIG. 16A). Then using the patterned portion as a mask, the second insulation film 104, anti-reflection film 105 and photo resist 106 are removed, so as to generate a pattern of which ratio of line and space is 1:3 on the second insulation film 104 (see FIG. 16B). Then the third insulation film 107 is layered on the patterned second insulation film 104 (see FIG. 17A), and the third insulation film 107 is etched until the surface of the second insulation film 104 is exposed, whereby the side wall layer constituted by the third insulation film 107 is formed on the side wall of the second insulation film 104 (see FIG. 17B). By removing the second insulation film 104, a repeated pattern having a half pitch of a mask (pattern), of which ratio of the line portion and space portion is 1:3 (third insulation film 107), is formed. Such a repeated pattern having a half pitch of a repeat pitch, that is generated based on the mask that has a pattern with a predetermined repeat pitch, may be used. In this case, if the film deposition conditions are not appropriate when the third insulation film 107 is deposited, the film thickness of the third insulation film 107 becomes different at the left and right of the second insulation film 104, and the line width of the repeated pattern becomes uneven. Such a defect can also be detected by the present embodiment.

In the present embodiment, an example when the linearly polarized light L1 is p-polarized light was described, but the present invention is not limited to this. For example, s-polarized light instead of p-polarized light may be used. S-polarized light is a linearly polarized light of which plane of vibration is vertical to the incident plane. Therefore, as shown in FIG. 10, if the repeat direction (X direction) of the repeated pattern 12 on the wafer 10 is set to be a 45° angle from the incident plane A2 of the linearly polarized light L1, which is s-polarized light, the angle formed by the direction of the plane of vibration of the s-polarized light on the surface of the wafer 10 and the repeat direction (X direction) of the repeated pattern 12 is also set to 45°. The p-polarized light has an advantage of acquiring defect information related to the edge profile of the line portion 2A of the repeated pattern 12. And the s-polarized light has an advantage of improving the SN ratio by efficiently reflecting the defect information on the surface of the wafer 10.

Instead of p-polarized light or s-polarized light, a linearly polarized light of which plane of vibration has an arbitrary inclination with respect to the incident plane can also be used. In this case, it is preferable that the repeat direction (X direction) of the repeated pattern 12 is set to an angle other than 45° with respect to the incident plane of the linearly polarized light L1, setting the angle formed by the direction of the plane of vibration of the linearly polarized light L1 on the surface of the wafer 10 and the repeat direction (X direction) of the repeated pattern 12 to 45°. This angle, however, is not limited to 45°, and depending on the pattern, the ratio of image signal intensity of a non-defective product shot and defective product shot may become large in a position shifted from 45°, whether p-polarized light is used or s-polarized light is used.

In the above embodiment, the linearly polarized light L1 is generated using the illumination light from the illumination unit 21 and the illumination side polarization filter 22, but the present invention is not limited to this, and if a laser, to supply linearly polarized light, is used as a light source, the illumination side polarization filter 22 is unnecessary.

What is claimed is:

1. A surface inspection method that inspects a surface of a target substrate having a repeated pattern with half pitch of a predetermined repeat pitch, in which a first half pattern having the predetermined repeat pitch and a second half pattern located in a position shifted from the first half pattern by half of the repeat pitch and having an approximately same profile as the first half pattern, are formed at least in partially different steps, comprising:
    a light applying step that applies an inspection light to a surface of the target substrate;
    a diffracted light detecting step that detects a diffracted light from the surface of the target substrate to which the inspection light has been applied; and
    a diffraction inspecting step that inspects whether a defect is present in the repeated pattern based on the diffracted light detected in the diffracted light detecting step; wherein
    the diffracted light detecting step further detects the diffracted light corresponding to a pattern having a pitch multiplied by an integer equal to or greater than 2 with respect to the half pitch of the repeat pitch.

2. The surface inspection method according to claim 1, further comprising:
    a polarized light applying step that applies a first linearly polarized light to the surface of the target substrate;
    an extracting step that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;
    a polarized light component detecting step that detects a light quantity of the second linearly polarized light component;
    a PER inspecting step that inspects whether a defect is present in the repeated pattern based on the light quantity of the second linearly polarized light component detected in the polarized light component detecting step; and
    a defect detecting step that detects a position shift defect and a line width shift defect in the repeated pattern, respectively, based on the inspection results in the diffraction inspecting step and the PER inspecting step.

3. The surface inspection method according to claim 2, wherein
    the defect detecting step calculates a line width shift amount in the repeated pattern based on the light quantity of the second linearly polarized light component detected in the polarized light component detecting step, determines that the repeated pattern has the line width shift defect if the calculated line width shift amount is greater than a first threshold, calculates a position shift amount in the repeated pattern based on the calculated line width shift amount and the diffracted light detected in the diffracted light detecting step, and determines that the repeated pattern has the position shift defect if the calculated position shift amount is greater than a second threshold.

4. A surface inspection method that inspects a surface of a target substrate having a repeated pattern with half or less pitch of a predetermined repeat pitch which is formed according to a mask having a pattern profile with the predetermined repeat pitch, comprising:
    a light applying step that applies an inspection light to the surface of the target substrate;
    a diffracted light detecting step that detects a diffracted light from the surface of the target substrate to which the inspection light has been applied; and
    a diffraction inspecting step that inspects whether a defect is present in the repeated pattern based on the diffracted light detected in the diffracted light detecting step; wherein
    the diffracted light detecting step further detects the diffracted light corresponding to a pattern having a pitch multiplied by an integer equal to or greater than 2 with respect to the repeated pattern with half or less pitch of the repeat pitch.

5. The surface inspection method according to claim 4, further comprising:

a polarized light applying step that applies a first linearly polarized light to the surface of the target substrate;

an extracting step that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;

a polarized light component detecting step that detects a light quantity of the second linearly polarized light component;

a PER inspecting step that inspects whether a defect is present in the repeated pattern based on the light quantity of the second linearly polarized light component detected in the polarized light component detecting step; and a defect detecting step that detects a position shift defect and a line width shift defect in the repeated pattern, respectively, based on the inspection results in the diffraction inspecting step and the PER inspecting step.

6. The surface inspection method according to claim 5, wherein
the defect detecting step calculates a line width shift amount in the repeated pattern based on the light quantity of the second linearly polarized light component detected in the polarized light component detecting step, determines that the repeated pattern has the line width shift defect if the calculated line width shift amount is greater than a first threshold, calculates a position shift amount in the repeated pattern based on the calculated line width shift amount and the diffracted light detected in the diffraction light detecting step, and determines that the repeated pattern has the position shift defect if the calculated position shift amount is greater than a second threshold.

7. A surface inspection method, comprising:
a light applying step that applies an inspection light to a surface of a target substrate on which a repeated pattern is formed;
a diffracted light detecting step that detects a diffracted light from the surface of the target substrate to which the inspection light has been applied;
a diffraction inspecting step that applies a first linearly polarized light to the surface of the target substrate;
a polarized light applying step that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;
an extracting step that detects a light quantity of the second linearly polarized light component; and
a polarized light component detecting step that inspects whether a defect is present in the repeated pattern based on the diffracted light detected in the diffracted light detecting step and the light quantity of the second linearly polarized light component detected in the extracting step.

8. The surface inspection method according to claim 7, wherein
the polarized light component detecting step calculates a line width shift amount in the repeated pattern based on the light quantity of the second linearly polarized light component detected in the extracting step, determines that the repeated pattern has the line width shift defect if the calculated line width shift amount is greater than a first threshold, calculates a position shift amount in the repeated pattern based on the calculated line width shift amount and the diffracted light detected in the diffracted light detecting step, and determines that the repeated pattern has the position shift defect if the calculated position shift amount is greater than a second threshold.

9. A surface inspection device that inspects a surface of a target substrate having a repeated pattern with half pitch of a predetermined repeat pitch, in which a first half pattern having the predetermined repeat pitch and a second half pattern located in a position shifted from the first half pattern by half of the repeat pitch and having an approximately same profile as the first half pattern, are formed in at least partially different steps, comprising:
an inspection light illumination unit that applies an inspection light to a surface of the target substrate;
a diffracted light detection unit that detects a diffracted light from the surface of the target substrate to which the inspection light has been applied; and
a diffracted light inspection unit that inspects whether a defect is present in the repeated pattern based on the diffracted light detected in the diffracted light detection unit; wherein the diffractive light detection unit detects the diffracted light corresponding to a pattern having a pitch multiplied by an integer equal to or greater than 2 with respect to the half pitch of the repeat pitch.

10. The surface inspection device according to claim 9, further comprising:
a polarized light illumination unit that applies a first linearly polarized light to the surface of the target substrate;
a polarized light extraction unit that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;
a polarized light detection unit that detects a light quantity of the second linearly polarized light component;
a polarized light inspection unit that inspects whether a defect is present in the repeated pattern based on the light quantity of the second linearly polarized light component detected by the polarized light detection unit; and
decision unit that detects a position shift defect and a line width shift defect in the repeated pattern, respectively, based on the inspection results by the diffracted light inspection unit and the polarized light inspection unit.

11. The surface inspection device according to claim 10, wherein
the decision unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

12. A surface inspection device that inspects a surface of a target substrate having a repeated pattern with half or less pitch of a predetermined repeat pitch which is formed according to a mask having a pattern profile with the predetermined repeat pitch, comprising:

an inspection light illumination unit that applies an inspection light to the surface of the target substrate;

a diffracted light detection unit that detects a diffracted light from the surface of the target substrate to which the inspection light has been applied; and a diffracted light inspection unit that inspects whether a defect is present in the repeated pattern based on the diffracted light detected by the diffracted light detection unit; wherein the diffractive light detection unit detects the diffracted light corresponding to a pattern having a pitch multiplied by an integer equal to or greater than 2 with respect to the repeated pattern with half or less pitch of the repeat pitch.

13. The surface inspection device according to claim 12, further comprising:

a polarized light illumination unit that applies a first linearly polarized light to the surface of the target substrate;

a polarized light extraction unit that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;

a polarized light detection unit that detects a light quantity of the second linearly polarized light component;

a polarized light inspection unit that inspects whether a defect is present in the repeated pattern based on the light quantity of the second linearly polarized light component detected by the polarized light detection unit; and a decision unit that detects a position shift defect and a line width shift defect in the repeated pattern, respectively, based on the inspection results by the diffracted light inspection unit and the polarized light inspection unit.

14. The surface inspection device according to claim 13, wherein the decision unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

15. A surface inspection device, comprising:

an inspection light illumination unit that applies an inspection light to a surface of a target substrate on which a repeated pattern is formed;

a diffracted light detection unit that detects a diffracted light from the surface of the target substrate to which the inspection light has been applied;

a polarized light illumination unit that applies a first linearly polarized light to the surface of the target substrate;

a polarized light extraction unit that extracts a second linearly polarized light component, wherein a direction of vibration of the second linearly polarized light is different from a direction of vibration of the first linearly polarized light, and is also different from a direction of vibration of a reflected light from the surface of the target substrate to which the first linearly polarized light has been applied;

a polarized light detection unit that detects a light quantity of the second linearly polarized light component; and an inspection unit that inspects whether a defect is present in the repeated pattern based on the diffracted light detected by the diffracted light detection unit and the light quantity of the second linearly polarized light component detected by the polarized light detection unit.

16. The surface inspection device according to claim 15, wherein the inspection unit calculates a line width shift amount in the repeated pattern based on the light quantity of the second linearly polarized light component detected by the polarized light detection unit, determines that the repeated pattern has the line width shift defect if the calculated line width shift amount is greater than a first threshold, calculates a position shift amount in the repeated pattern based on the calculated line width shift amount and the diffracted light detected by the diffracted light detection unit, and determines that the repeated pattern has the position shift defect if the calculated position shift amount is greater than a second threshold.

17. The surface inspection method according to claim 1, further comprising:

a pre-inspection step that inspects the surface of the target substrate in a stage when only the first half pattern of the repeated pattern is formed on the surface of the target substrate, wherein the surface of the target substrate is inspected after the second half pattern is formed on the surface of the target substrate that has been determined as a non-defective product in the pre-inspection step.

18. The surface inspection method according to claim 2, further comprising:

a pre-inspection step that inspects the surface of the target substrate in a stage when only the first half pattern of the repeated pattern is formed on the surface of the target substrate, wherein the surface of the target substrate is inspected after the second half pattern is formed on the surface of the target substrate that has been determined as a non-defective product in the pre-inspection step.

19. The surface inspection method according to claim 3, further comprising:

a pre-inspection step that inspects the surface of the target substrate in a stage when only the first half pattern of the repeated pattern is formed on the surface of the target substrate, wherein the surface of the target substrate is inspected after the second half pattern is formed on the surface of the target substrate that has been determined as a non-defective product in the pre-inspection step.

* * * * *